(12) United States Patent
Bak

(10) Patent No.: US 8,892,184 B2
(45) Date of Patent: Nov. 18, 2014

(54) SYSTEMS AND METHODS FOR REDUCING INTERFERENCE IN A DUAL MODALITY IMAGING SYSTEM

(75) Inventor: Donald J. Bak, Streamwood, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1067 days.

(21) Appl. No.: 12/906,436

(22) Filed: Oct. 18, 2010

(65) Prior Publication Data

US 2012/0095321 A1    Apr. 19, 2012

(51) Int. Cl.
*A61B 5/055* (2006.01)
*A61B 6/00* (2006.01)
*A61B 6/03* (2006.01)

(52) U.S. Cl.
CPC ............. *A61B 5/055* (2013.01); *A61B 6/4417* (2013.01); *A61B 6/5247* (2013.01); *A61B 6/037* (2013.01)
USPC ........................................................ 600/411

(58) Field of Classification Search
CPC . A61B 6/4417; A61B 6/5247; G01R 33/4808
USPC ........................................................ 600/411
See application file for complete search history.

(56) References Cited

U.S. PATENT DOCUMENTS

| | | | |
|---|---|---|---|
| 5,451,785 A | | 9/1995 | Faris |
| 5,529,068 A | * | 6/1996 | Hoenninger et al. ......... 600/413 |
| 5,796,500 A | | 8/1998 | Hart |
| 5,808,376 A | | 9/1998 | Gordon et al. |
| 5,936,739 A | | 8/1999 | Cameron et al. |
| 5,976,088 A | | 11/1999 | Urbano et al. |
| 6,056,691 A | | 5/2000 | Urbano et al. |
| 6,086,537 A | | 7/2000 | Urbano et al. |
| 6,090,332 A | | 7/2000 | Marder et al. |
| 6,228,030 B1 | | 5/2001 | Urbano et al. |
| 6,402,994 B1 | | 6/2002 | Marder et al. |
| 6,477,398 B1 | | 11/2002 | Mills |
| 6,578,002 B1 | | 6/2003 | Derzay et al. |
| 6,590,215 B2 | | 7/2003 | Nygard et al. |
| 6,598,011 B1 | | 7/2003 | Howards Koritzinsky et al. |
| 6,606,583 B1 | | 8/2003 | Sternberg et al. |
| 6,639,939 B1 | | 10/2003 | Naden et al. |
| 6,643,317 B1 | | 11/2003 | Blumer |
| 6,643,334 B1 | | 11/2003 | Limberg |
| 6,680,750 B1 | | 1/2004 | Tournier et al. |
| 6,683,105 B2 | | 1/2004 | Greig et al. |
| 6,690,742 B2 | | 2/2004 | Chan |
| 6,697,416 B1 | | 2/2004 | Jennings |
| RE38,456 E | | 3/2004 | Patel et al. |
| 6,741,529 B1 | | 5/2004 | Getreuer |

(Continued)

*Primary Examiner* — Unsu Jung
*Assistant Examiner* — Daniel Huntley
(74) *Attorney, Agent, or Firm* — Peter Kendall

(57) ABSTRACT

A magnetic resonance (MR)-positron emission tomography (PET) device dual modality system includes a dual modality detector system, conductors, and a PET processing device. The dual modality detector system includes a plurality of PET detector device having a framing recovery device and PET detectors, and an MR detector device having a magnetic resonance (MR) receiver. The conductors are electrically connected to the PET detectors. The PET processing device transmits modulated timing and frame synchronization signals to the PET detectors via the conductors and the framing recovery device. The frame synchronization signal is missing one or more framing signals, thereby reducing a spectral radiation of the conductors that causes interference to the MR receiver of the MR detector device. The framing recovery device detects the timing and frame synchronization signals and recovers the one or more missing framing signals.

20 Claims, 8 Drawing Sheets

(56) References Cited

U.S. PATENT DOCUMENTS

| | | |
|---|---|---|
| 6,760,078 B2 | 7/2004 | Limberg |
| 6,762,784 B2 | 7/2004 | Skillman |
| 6,791,090 B2 | 9/2004 | Lin et al. |
| 6,804,304 B1 | 10/2004 | Chan |
| 6,812,824 B1 | 11/2004 | Goldinger et al. |
| 6,828,564 B2 | 12/2004 | Worstell et al. |
| 6,834,073 B1 | 12/2004 | Miller et al. |
| 6,844,963 B2 | 1/2005 | Iketaki et al. |
| 6,853,690 B1 | 2/2005 | Sorrells et al. |
| 6,856,350 B2 | 2/2005 | Orava et al. |
| 6,859,506 B1 | 2/2005 | McCorkle |
| 6,875,176 B2 | 4/2005 | Mourad et al. |
| 6,882,217 B1 | 4/2005 | Mueller |
| 6,895,046 B1 | 5/2005 | Willis et al. |
| 6,895,507 B1 | 5/2005 | Teppler |
| 6,897,687 B2 | 5/2005 | Cafaro et al. |
| 6,898,709 B1 | 5/2005 | Teppler |
| 6,901,337 B2 | 5/2005 | Tanaka et al. |
| 6,901,371 B1 | 5/2005 | Koritzinsky et al. |
| 6,904,110 B2 | 6/2005 | Trans et al. |
| 6,906,559 B2 | 6/2005 | Tumer |
| 6,907,280 B2 | 6/2005 | Becerra et al. |
| 6,926,898 B2 | 8/2005 | Rosen et al. |
| 6,931,073 B2 | 8/2005 | Chan |
| 6,954,490 B2 | 10/2005 | Chan |
| 6,963,616 B2 | 11/2005 | Chan |
| 6,963,770 B2 | 11/2005 | Scarantino et al. |
| 6,963,771 B2 | 11/2005 | Scarantino et al. |
| 6,966,040 B2 | 11/2005 | Ismailov |
| 6,975,629 B2 | 12/2005 | Welin |
| 6,977,380 B2 | 12/2005 | Chowdhury et al. |
| 6,984,734 B2 | 1/2006 | Sessler et al. |
| 6,988,074 B2 | 1/2006 | Koritzinsky et al. |
| 6,992,295 B2 | 1/2006 | Romanov et al. |
| 6,992,762 B2 | 1/2006 | Long et al. |
| 6,993,378 B2 | 1/2006 | Wiederhold et al. |
| 7,006,553 B1 | 2/2006 | McCorkle |
| 7,010,340 B2 | 3/2006 | Scarantino et al. |
| 7,022,077 B2 | 4/2006 | Mourad et al. |
| 7,022,995 B2 | 4/2006 | Tumer |
| 7,034,310 B2 | 4/2006 | Tumer |
| 7,035,698 B2 | 4/2006 | Johnson et al. |
| 7,038,732 B1 | 5/2006 | Limberg et al. |
| 7,050,419 B2 | 5/2006 | Azenkot et al. |
| 7,051,309 B1 | 5/2006 | Crosetto |
| 7,054,296 B1 | 5/2006 | Sorrells et al. |
| 7,060,983 B2 | 6/2006 | Tumer |
| 7,077,569 B1 | 7/2006 | Tybinkowski et al. |
| 7,089,158 B2 | 8/2006 | Sternberg et al. |
| 7,091,489 B2 | 8/2006 | Schlyer et al. |
| 7,101,339 B2 | 9/2006 | Daum et al. |
| 7,108,424 B2 | 9/2006 | Heumann et al. |
| 7,110,435 B1 | 9/2006 | Sorrells et al. |
| 7,115,766 B2 | 10/2006 | Mulhollard et al. |
| 7,115,875 B1 | 10/2006 | Worstell |
| 7,116,749 B2 | 10/2006 | Besson |
| 7,120,486 B2 | 10/2006 | Leuthardt et al. |
| 7,126,126 B2 | 10/2006 | Schyler et al. |
| 7,127,499 B1 | 10/2006 | Accardi et al. |
| 7,129,495 B2 | 10/2006 | Williams et al. |
| 7,141,547 B2 | 11/2006 | Rosen et al. |
| 7,144,370 B2 | 12/2006 | Fomitchov |
| 7,149,565 B2 | 12/2006 | Kojima et al. |
| 7,158,692 B2 | 1/2007 | Chalana et al. |
| 7,164,699 B1 | 1/2007 | Braun |
| 7,171,252 B1 | 1/2007 | Scarantino et al. |
| 7,175,988 B2 | 2/2007 | Roschke et al. |
| 7,177,675 B2 | 2/2007 | Suffin et al. |
| 7,179,449 B2 | 2/2007 | Lanza et al. |
| 7,180,074 B1 | 2/2007 | Crosetto |
| 7,180,951 B2 | 2/2007 | Chan |
| 7,187,790 B2 | 3/2007 | Sabol et al. |
| 7,187,794 B2 | 3/2007 | Liang et al. |
| 7,190,991 B2 | 3/2007 | Cable et al. |
| 7,194,313 B2 | 3/2007 | Libbus |
| 7,211,250 B2 | 5/2007 | Segal et al. |
| 7,215,931 B2 | 5/2007 | Snyder et al. |
| 7,215,991 B2 | 5/2007 | Besson et al. |
| 7,217,928 B2 | 5/2007 | Crosetto |
| 7,218,705 B2 | 5/2007 | Xue et al. |
| 7,219,032 B2 | 5/2007 | Spiesberger |
| 7,224,349 B2 | 5/2007 | Irie |
| 7,232,667 B2 | 6/2007 | Ruben et al. |
| 7,234,064 B2 | 6/2007 | Menschik et al. |
| 7,238,667 B2 | 7/2007 | Rosen et al. |
| 7,238,943 B2 | 7/2007 | Wong et al. |
| 7,239,257 B1 | 7/2007 | Alexander et al. |
| 7,239,855 B2 | 7/2007 | Matsui et al. |
| 7,251,523 B2 | 7/2007 | Kojima et al. |
| 7,252,638 B2 | 8/2007 | Kahn et al. |
| 7,258,687 B2 | 8/2007 | Friedman et al. |
| 7,266,176 B2 | 9/2007 | Allison et al. |
| 7,267,978 B1 | 9/2007 | Carey et al. |
| 7,280,710 B1 | 10/2007 | Castro-Pareja et al. |
| 7,282,944 B2 | 10/2007 | Gunn et al. |
| 7,283,607 B2 | 10/2007 | Sommer |
| 7,283,654 B2 | 10/2007 | McLain |
| 7,286,867 B2 | 10/2007 | Schlyer et al. |
| 7,286,871 B2 | 10/2007 | Cohen |
| 7,295,048 B2 | 11/2007 | Gilliland |
| 7,301,151 B2 | 11/2007 | Rutten et al. |
| 7,305,039 B2 | 12/2007 | Chan |
| 7,306,593 B2 | 12/2007 | Keidar et al. |
| 7,307,630 B2 | 12/2007 | Lessieux |
| 7,308,299 B2 | 12/2007 | Burrell et al. |
| 7,309,315 B2 | 12/2007 | Kullok et al. |
| 7,313,161 B2 | 12/2007 | Chen et al. |
| 7,315,564 B2 | 1/2008 | McCorkle |
| 7,323,688 B2 | 1/2008 | Joung |
| 7,327,872 B2 | 2/2008 | Vaillant et al. |
| 7,329,009 B2 | 2/2008 | Monch et al. |
| 7,330,535 B2 | 2/2008 | Arenson et al. |
| 7,336,769 B2 | 2/2008 | Arenson et al. |
| 7,338,455 B2 | 3/2008 | White et al. |
| 7,340,180 B2 | 3/2008 | Farmer et al. |
| 7,343,195 B2 | 3/2008 | Strommer et al. |
| 7,344,306 B2 | 3/2008 | Hsieh et al. |
| 7,345,284 B2 | 3/2008 | Tumer |
| 7,346,381 B2 | 3/2008 | Okerlund et al. |
| 7,353,065 B2 | 4/2008 | Morrell |
| 7,356,178 B2 | 4/2008 | Ziel et al. |
| 7,357,934 B2 | 4/2008 | Donovan et al. |
| 7,359,535 B2 | 4/2008 | Salla et al. |
| 7,362,525 B2 | 4/2008 | Norton, Jr. |
| 7,363,191 B2 | 4/2008 | Spiesberger |
| 7,364,730 B2 | 4/2008 | Pardo-Fernandez et al. |
| 7,364,845 B2 | 4/2008 | Pardo-Fernandez et al. |
| 7,367,807 B1 | 5/2008 | Pennebaker |
| 7,371,370 B2 | 5/2008 | Sarkar et al. |
| 7,371,517 B2 | 5/2008 | Evans et al. |
| 7,371,575 B2 | 5/2008 | Kale et al. |
| 7,371,811 B2 | 5/2008 | Cohen et al. |
| 7,372,984 B2 | 5/2008 | Dickinson et al. |
| 7,376,903 B2 | 5/2008 | Morita et al. |
| 7,379,769 B2 | 5/2008 | Piron et al. |
| 7,384,638 B2 | 6/2008 | Bhatia et al. |
| 7,385,034 B2 | 6/2008 | Edwards et al. |
| 7,385,395 B2 | 6/2008 | Pines et al. |
| 7,386,339 B2 | 6/2008 | Strommer et al. |
| 7,389,137 B2 | 6/2008 | Helfer et al. |
| 7,390,625 B2 | 6/2008 | Ichijo |
| 7,392,491 B2 | 6/2008 | Ismailov |
| 7,393,661 B2 | 7/2008 | Fruebis et al. |
| 7,393,663 B2 | 7/2008 | Edwards et al. |
| 7,393,924 B2 | 7/2008 | Vitaliano et al. |
| 7,393,934 B2 | 7/2008 | Roschke et al. |
| 7,400,093 B2 | 7/2008 | Salop |
| 7,400,696 B2 | 7/2008 | Chen et al. |
| 7,401,057 B2 | 7/2008 | Eder |
| 7,402,304 B2 | 7/2008 | Sarkar et al. |
| 7,402,393 B2 | 7/2008 | Chumakov et al. |
| 7,402,575 B2 | 7/2008 | Mink et al. |
| 7,403,638 B2 | 7/2008 | Jeung et al. |
| 7,403,805 B2 | 7/2008 | Abreu |

(56) References Cited

U.S. PATENT DOCUMENTS

| | | |
|---|---|---|
| 7,403,820 B2 | 7/2008 | DiLorenzo |
| 7,404,950 B2 | 7/2008 | Spencer et al. |
| 7,405,286 B2 | 7/2008 | Olson et al. |
| 7,405,494 B2 | 7/2008 | Tassitino, Jr. et al. |
| 7,409,557 B2 | 8/2008 | Teppler |
| 7,411,393 B2 | 8/2008 | Zhang |
| 7,412,084 B2 | 8/2008 | Jerebko |
| 7,415,304 B2 | 8/2008 | Rowlandson et al. |
| 7,419,674 B2 | 9/2008 | Chulay et al. |
| 7,420,100 B2 | 9/2008 | Olson et al. |
| 7,425,325 B2 | 9/2008 | Sprecher et al. |
| 7,425,337 B2 | 9/2008 | Smith et al. |
| 7,425,436 B2 | 9/2008 | Darzins et al. |
| 7,425,607 B2 | 9/2008 | Henderson et al. |
| 7,427,482 B2 | 9/2008 | Blumenfeld et al. |
| 7,427,489 B1 | 9/2008 | Kay et al. |
| 7,429,472 B2 | 9/2008 | Darzins et al. |
| 7,429,479 B2 | 9/2008 | Harding |
| 7,430,257 B1 | 9/2008 | Shattil |
| 7,430,309 B2 | 9/2008 | Harel et al. |
| 7,432,056 B2 | 10/2008 | Blumenfeld et al. |
| 7,442,381 B2 | 10/2008 | Smith et al. |
| 7,444,011 B2 | 10/2008 | Pan et al. |
| 7,445,930 B2 | 11/2008 | Zhang et al. |
| 7,446,526 B2 | 11/2008 | Cunningham et al. |
| 7,449,170 B2 | 11/2008 | Regnier et al. |
| 7,449,543 B2 | 11/2008 | Bihain et al. |
| 7,450,229 B2 | 11/2008 | Ortyn |
| 7,451,005 B2 | 11/2008 | Hoffberg et al. |
| 7,454,248 B2 | 11/2008 | Burrell et al. |
| 7,455,453 B2 | 11/2008 | Lauritsch et al. |
| 7,455,978 B2 | 11/2008 | Thomas et al. |
| 7,459,293 B2 | 12/2008 | Sprecher et al. |
| 7,459,433 B2 | 12/2008 | Lucas et al. |
| 7,459,688 B2 | 12/2008 | Aoki |
| 7,460,223 B2 | 12/2008 | Harding |
| 7,460,248 B2 | 12/2008 | Kurtz et al. |
| 7,460,906 B2 | 12/2008 | Libbus |
| 7,461,045 B1 | 12/2008 | Chaovalitwongse et al. |
| 7,463,919 B2 | 12/2008 | Hamilton et al. |
| 2010/0072986 A1* | 3/2010 | Lenglet .................. 324/207.11 |

* cited by examiner

SYSTEMS AND METHODS FOR REDUCING INTERFERENCE IN A DUAL MODALITY IMAGING SYSTEM

TECHNICAL FIELD

The present disclosure is generally related to nuclear medicine imaging and, more particularly, is related to systems and methods for reducing interference in a dual modality imaging system.

BACKGROUND

A magnetic resonance (MR)-positron emission tomography (PET) device dual modality system typically includes MR coils inserted within a ring of PET detectors. Each system, the MR system and PET system, is operated individually to obtain MR signals and PET signals, which are then combined to achieve high diagnostic accuracy. However, the electrical components of the PET system can generate interferences that interfere with the MR signals, resulting in diagnostic inaccuracy.

Desirable in the art is an improved MR-PET dual modality system that would reduce and/or eliminate the interference produced by the PET system of the MR-PET dual modality system.

SUMMARY

A magnetic resonance (MR)-positron emission tomography (PET) device dual modality system includes a dual modality detector system, conductors, and a PET processing device. The dual modality detector system includes a plurality of PET detector device having a framing recovery device and PET detectors, and an MR detector device having a magnetic resonance (MR) receiver. The conductors are electrically connected to the PET detectors. The PET processing device transmits modulated timing and frame synchronization signals to the PET detectors via the conductors and the framing recovery device. The frame synchronization signal is missing one or more framing signals, thereby reducing a spectral radiation of the conductors that causes interference to the MR receiver of the MR detector device. The framing recovery device detects the timing and frame synchronization signals and recovers the one or more missing framing signals.

Other systems, devices, methods, features of the present disclosure will be or will become apparent to one skilled in the art upon examination of the following figures and detailed description. It is intended that all such systems, devices, methods, features be included within the scope of the present disclosure, and be protected by the accompanying claims.

BRIEF DESCRIPTION OF DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, the reference numerals designate corresponding parts throughout the several views. While several embodiments are described in connection with these drawings, there is no intent to limit the disclosure to the embodiment or embodiments disclosed herein. On the contrary, the intent is to cover all alternatives, modifications, and equivalents.

DETAILED DESCRIPTION

Exemplary systems are first discussed with reference to the figures. Although these systems are described in detail, they are provided for purposes of illustration only and various modifications are feasible. After the exemplary systems are described, examples of flow diagrams of the systems are provided to explain the manner in which interference can be reduced in a dual modality imaging system.

Figure 1:
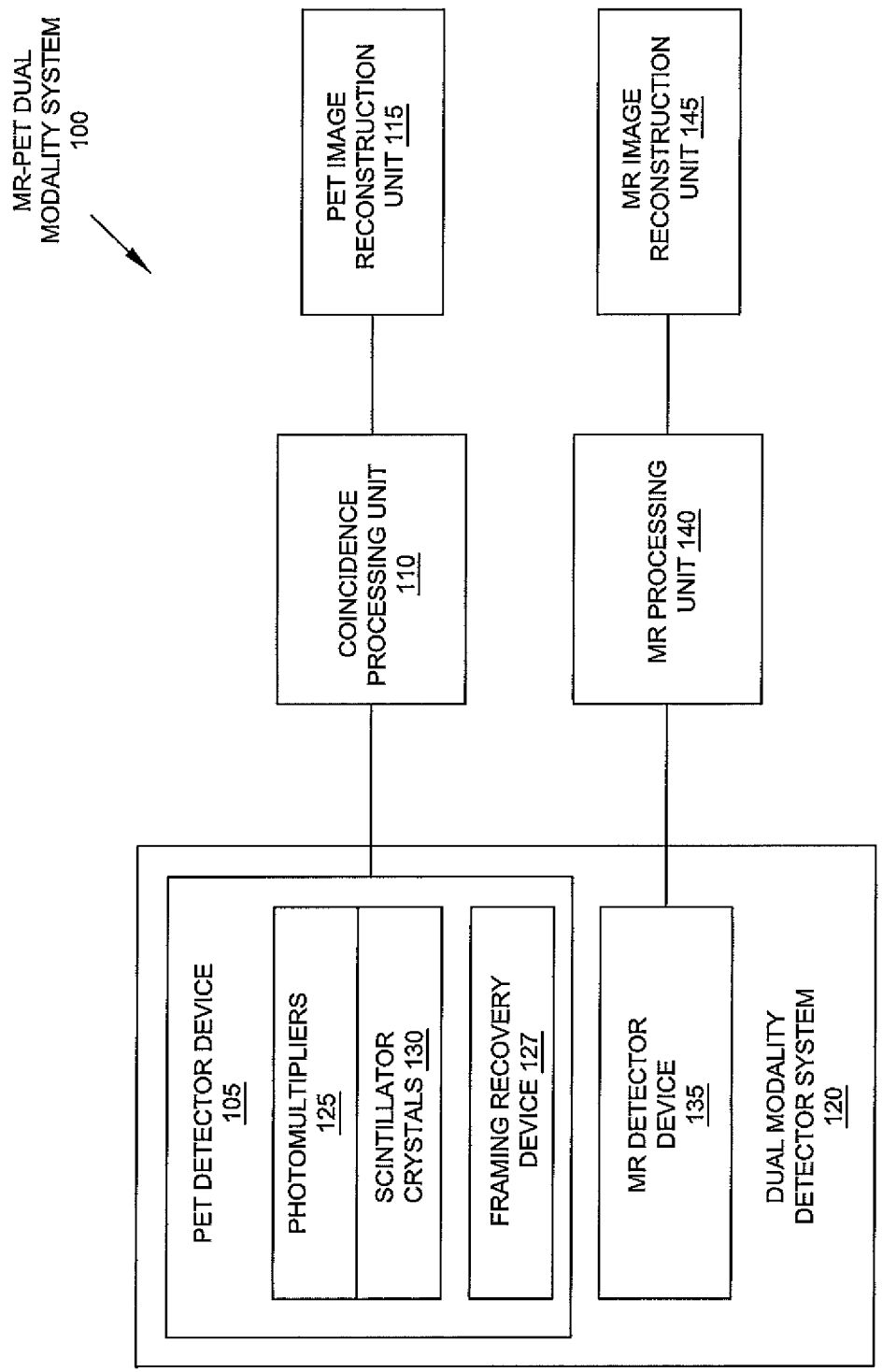
FIG. 1 is a high-level block diagram of a magnetic resonance (MR)-positron emission tomography (PET) device dual modality system having a framing recovery device in accordance with an embodiment of the present disclosure.

FIG. 1 is a high-level block diagram of a magnetic resonance (MR)-positron emission tomography (PET) device dual modality system 100 having a framing recovery device 127 in accordance with an embodiment of the present disclosure. In general, the MR-PET device dual modality system 100 includes a dual modality detector system 120 having a PET detector device 105 and an MR detector device 135.

The MR detector device 135 uses powerful magnets and radio waves. The magnetic field forces hydrogen atoms in a particular area of a, for example, human body, to line up in a certain way. When radio waves are sent toward the lined-up hydrogen atoms, the radio waves bounce back, and are detected by the MR detector device 135. The detected MR signals are recorded and processed by a MR processing unit 140. An MR image reconstruction unit 145 generates an image using the processed MR signals from the MR processing unit 140.

Figure 2:
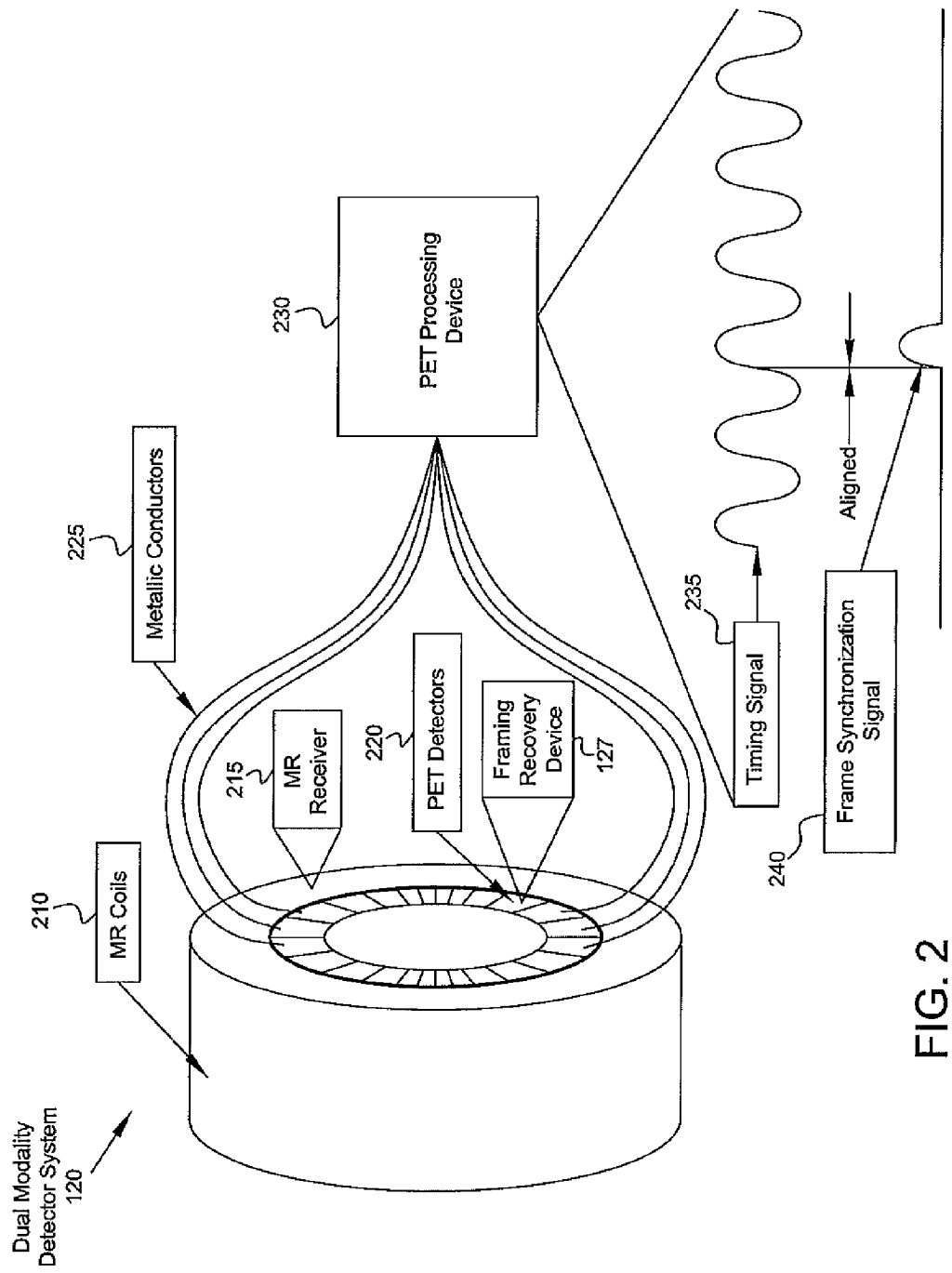
FIG. 2 is a block diagram of a magnetic resonance (MR)-positron emission tomography (PET) device dual modality system having a PET processing device that are coupled to a dual modality detector system via conductors in accordance with an embodiment of the present disclosure.

In general, different types of tissues send back different radio waves. When transmitted radio waves encounter tissues, the tissues reflect the radio waves back to the MR detector device 135. But in the process, the tissues change certain attributes of the radio waves and the way the radio waves are changed is determined by the type of tissues. For example, a healthy tissue and a cancerous tissue change the radio waves differently. The detection of these changes in the reflected radio waves allows a magnetic resonance imaging device to generate images that can differentiate healthy tissues from cancerous tissues. Referring to FIG. 2, the PET detector device 105 comprises a plurality of PET detectors 220 arranged in a ring configuration. Each of the PET detectors 220 includes a scintillator crystal 130 and an array of photomultipliers 125.

In general, a living subject is injected with a short-lived radioactive tracer isotope (e.g., usually into blood circulation) before conducting a positron emission tomography scan. The tracer isotope is for example fluorodeoxyglucose (FDG), which is a type of sugar. During the positron emission tomography scan, data is recorded from the tracer-concentrated tissue as the tracer isotope decays.

As the tracer-concentrated tissue undergoes positron emission decay, the tissue emits a positron, which is an antiparticle of the electron with opposite charge. The positron eventually collides with an electron, producing a pair of annihilation (gamma) photons moving in opposite directions. The pair of gamma photons are detected when they reach the scintillator crystals 130 in a pair of oppositely positioned PET detectors 220, each photon creating a burst of light in the scintillator crystal 130. The bursts of light generated by the pair of photons are then detected by the photomultipliers 125 in the PET detectors 220 and converted into electrical signals. These electrical signals are then processed by a coincidence processing unit 110 to determine whether the detected pair of photons originated from a coincident event. If so, the electrical signals are then sent to a PET image reconstruction unit 115 for reconstructing an image data using mathematical image reconstruction procedures.

In the dual modality detector system 120, the PET detector device 105 includes a framing recovery device 127 that facilitate reducing a spectral radiation of the conductors 225 (FIG. 2) that causes interference to the MR detector device 135. The framing recovery device 127 is further described in connection with FIGS. 2-5 and 9-12.

FIG. 2 is a block diagram of the magnetic resonance (MR)-positron emission tomography (PET) dual modality system 100 having a PET processing device 230 that is coupled to a dual modality detector system 120 via conductors 225 in accordance with an embodiment of the present disclosure. The MR-PET dual modality system 100 includes MR coils 210 inserted within a ring of PET detectors 220. For the PET modality, the coincident nuclear decay creates opposing events that are detected by the ring of PET detectors 220. The coincidence of these events must be precisely determined in time to identify these as occurring from a single decay. Each PET detector 220 contains a circuitry to amplify, digitize and time stamp each event. In general, timing and frame synchronization signals 235, 240 are transmitted from the PET processing device 230 to each PET detector 220 over (e.g., metallic) conductors 225. Although FIG. 2 shows only some PET detectors 220 being connected to metallic conductors 225 for illustration purposes, it can be appreciated by one skilled in the art that each PET detector 220 is connected to a metallic conductor 225. By using time matched distribution over the same media, the time stamp mechanism in the PET detectors 220 is able to determine within picoseconds the arrival of coincidence events. Additional conductors 225 that include, but not limited to, metallic materials or optical fiber are used in the opposite direction of the metallic conductor 225 to transfer the time stamped digitized event data to the PET processing 230.

The frequency of the timing signal 235 is generally selected to be above an operating range of a MR receiver 215 of the MR detector device 135 (FIG. 1) and at a single frequency to reduce the interference which would degrade the MR image. To reduce the harmonic content, the timing signal 235 is transmitted as a sinusoid on the metallic conductors 225. The frame synchronization signal 240 is generally aligned 245 with the timing signal 235.

In previous designs of the pet detector 220 system, the frame synchronization signal 240 is typically repeated every 8 cycles of the timing signal 235. The timing signal 235 is modulated with a framing signal 310 such that both signals 235, 310 can be transmitted coherently on the metallic conductors 225. One skilled in the art can appreciate that a variety of modulation method can be used to combine the signals. However, as a consequence of the modulation, the harmonic content of the radiation of the metallic conductors 225 is increased and likewise the interference to the MR receiver 215, reducing the quality and accuracy of the MR images.

In the present disclosure, the PET processing device 230 transmits modulated timing and frame synchronization signals 235, 240 to the PET detectors 220 via the conductors 225 and the framing recovery device 127. The frame synchronization signal 240 from the PET processing device 230 is missing one or more framing signals 315 (FIG. 3), thereby reducing a spectral radiation of the conductors 225 that causes interference to the MR receiver 215 of the MR detector device 135. The framing recovery device 127 detects the timing and frame synchronization signals 235, 240 and recovers the missing framing signals 315.

Figure 3:
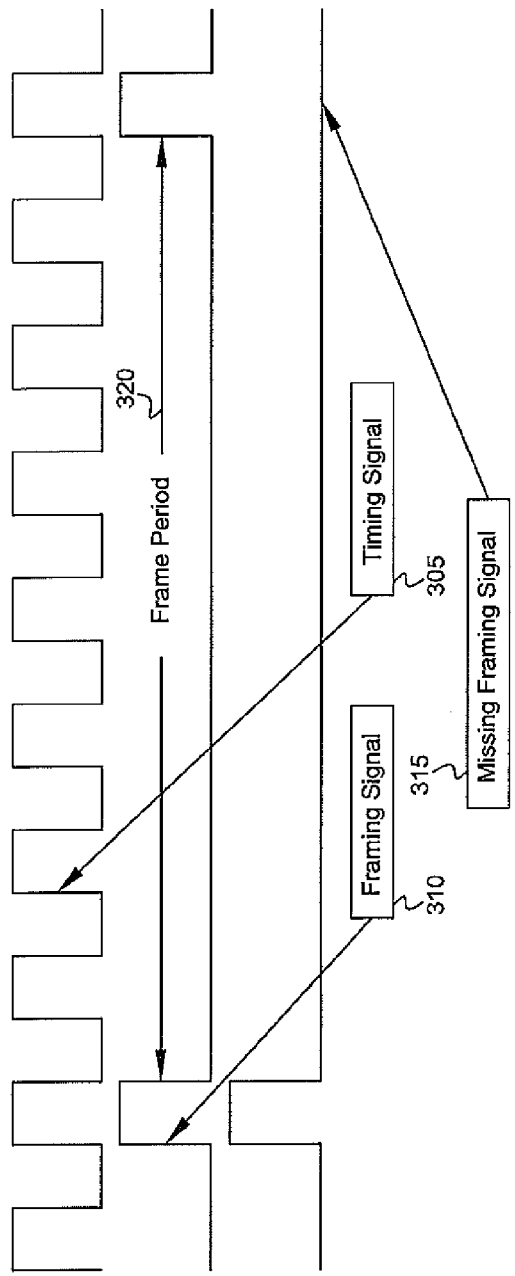
FIG. 3 is a waveform chart that illustrates an embodiment of operation of a PET processing device, such as that shown in FIG. 2.

FIG. 3 is a waveform chart that illustrates an embodiment of operation of a PET processing device 230, such as that shown in FIG. 2. The PET processing device 230 generates a timing signal 305 and a framing signal 310 in a frame period 320. The timing signal 305 is spectrally compatible with the MR receiver 215 despite the frame synchronization signal 240 is missing. However, most PET system requires a periodic framing signal 310 to operate. The PET processing device 230 reduces the frequency of the frame synchronization signal 240 that were present in the timing and frame synchronization signals 235, 240 by generating missing framing signal 315 during the MR imaging process, reducing the spectral radiation of the metallic conductors 225.

The PET processing device 230 modifies the frame synchronization signal 240 by reducing a period of generating the framing signals 310 by a predetermined factor, for example, once per 100 million transitions of the timing signal 235 or orders of magnitude larger. The reduced period of generating the framing signals can be called the "period of frame suppression." Such period of the frame suppression is a multiple of the frame period 320. For example if the frame period 320 is 8 cycles of the timing signal 305 the framing signal 310 could be suppressed for 800 million transitions of the timing signal 305. The timing signal 305 is a sinusoid with an infrequent modulation of the framing signal 310.

Figure 4:
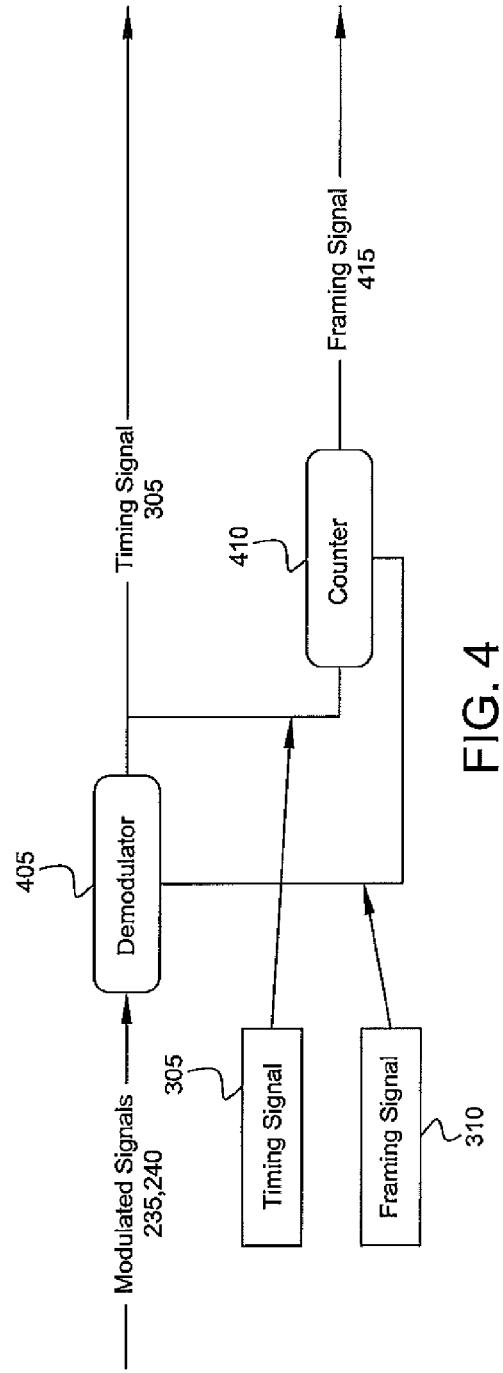
FIG. 4 is a high-level block diagram of a framing recovery device, such as that shown in FIG. 1.

FIG. 4 is a high-level block diagram of a framing recovery device 127, such as that shown in FIG. 1. The framing recovery device 127 can be located in the PET detector 220. The timing and frame synchronization signals 235, 240 are modulated by the PET processing device 230 (FIG. 2). The framing recovery device 127 includes a demodulator 405 that receives and demodulates the modulated timing and frame synchronization signals 235, 240 to separate the timing signal 305 and framing signal 310. These signals are transmitted to a counter 410 with a modulus of the frame period 320 (e.g. 8). The counter 410 recovers the missing framing signals 310 by generating a framing signal 310, for example, at every 8 cycles of the timing signal 305. In other words, the counter 410 detects the framing signal 310 and counts the cycles of the timing signal 305 from the detected framing signal 310. At every 8 cycles of the timing signal 305, the counter 410 generates a framing signal 310.

Figure 5:
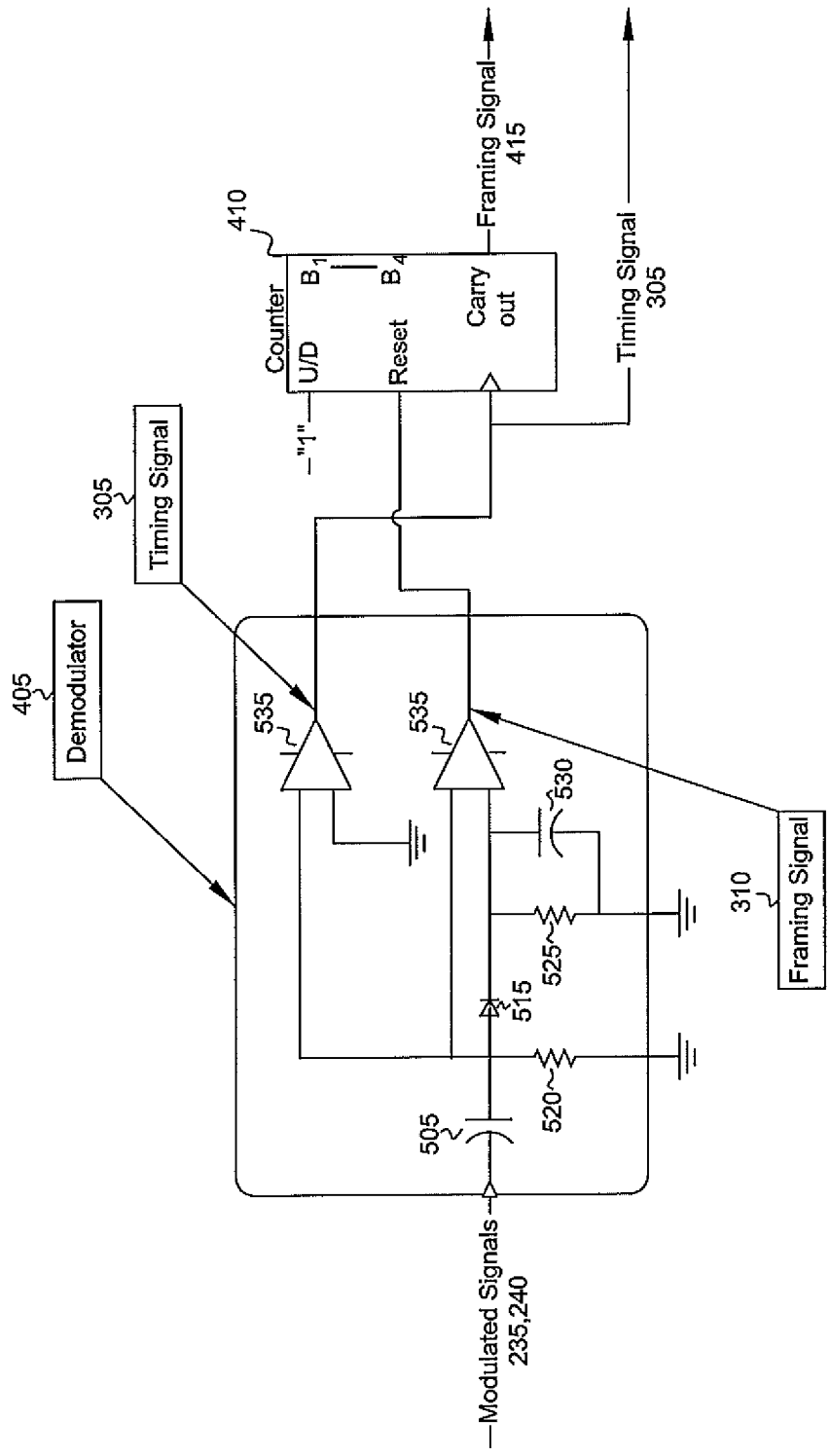
FIG. 5 is a detailed block diagram of a framing recovery device, such as that shown in FIG. 4.

FIG. 5 is a detailed block diagram of an exemplary framing recovery device 127, such as that shown in FIG. 4. It should be noted that the framing recovery device 127 can be implemented in many ways. The demodulator 405 of the framing recovery device 127 can be an amplitude demodulator 405 having, for example, amplifiers 510, 535 and capacitors 505, 530, resistors 520, 525, and a rectifier 515. The demodulator 405 is connected to a counter chip 410.

Figure 6:
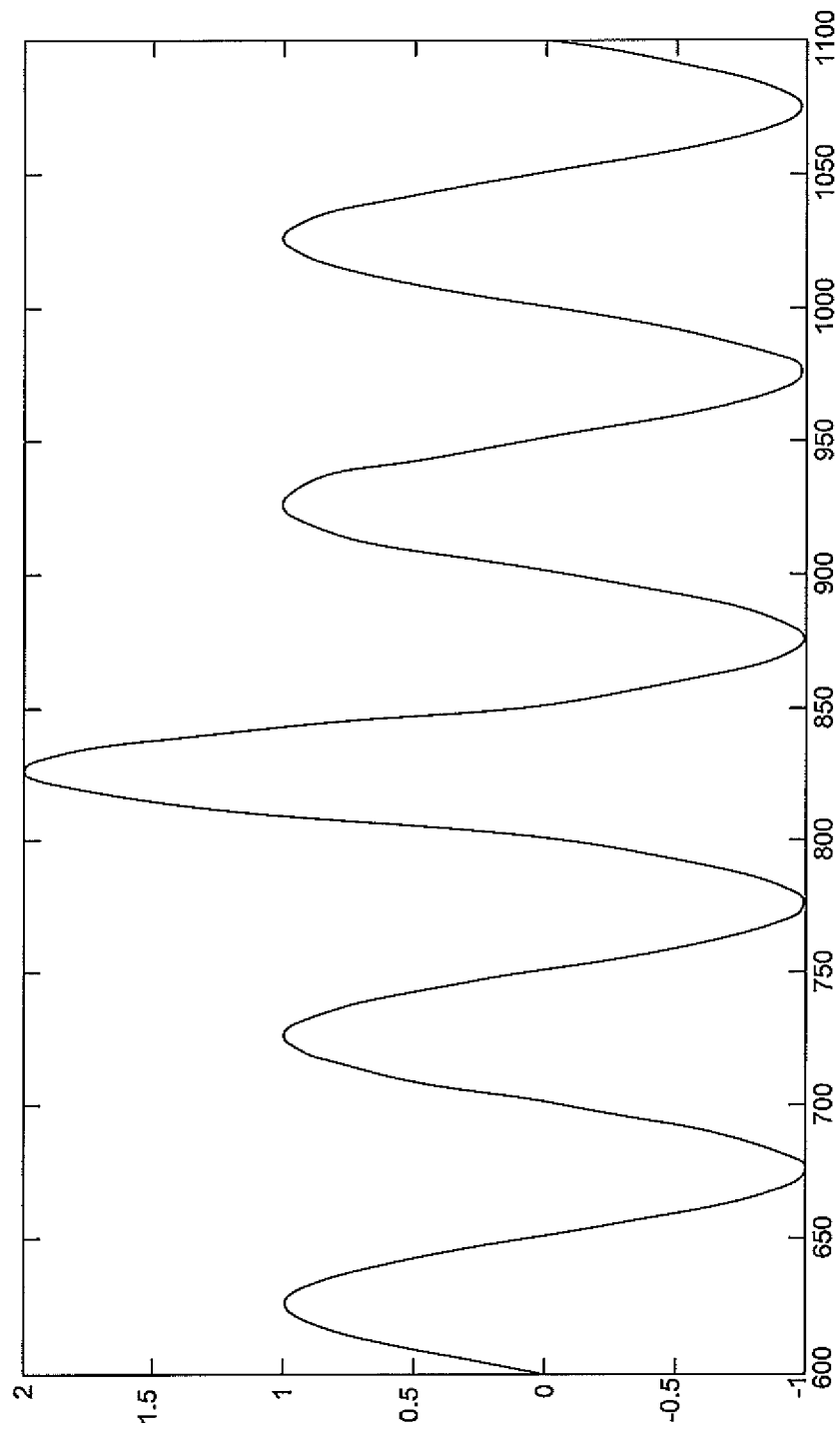
FIG. 6 is an expanded view of a sinusoid wave of un-modulated timing and frame synchronization signals.
Figure 7:
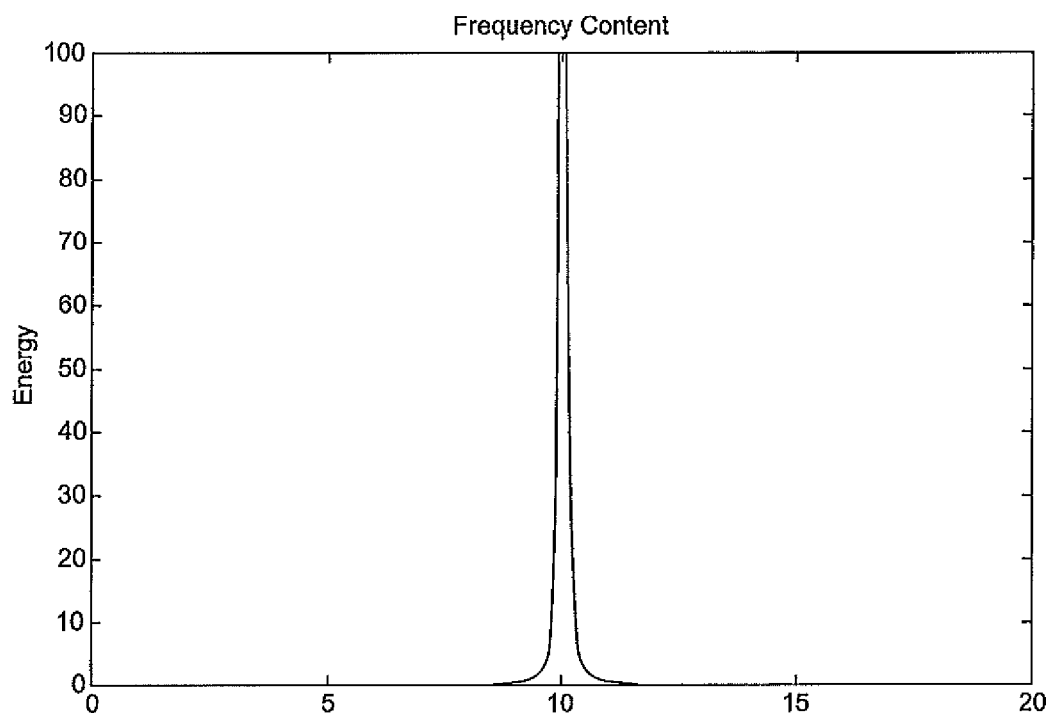
FIG. 7 is an expanded view of the frequency domain plot of un-modulated timing and frame synchronization signals, such as that shown in FIG. 6.
Figure 8:
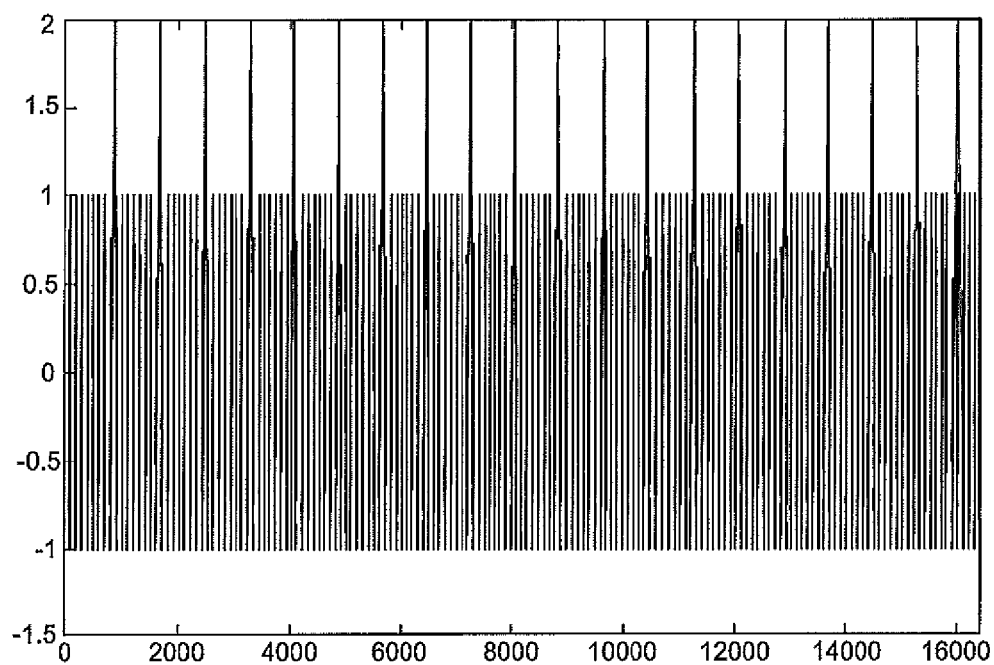
FIG. 8 is a sinusoid wave and a frame modulation that is generated, for example, every 8 cycles, in un-modulated timing and frame synchronization signals.
Figure 9:
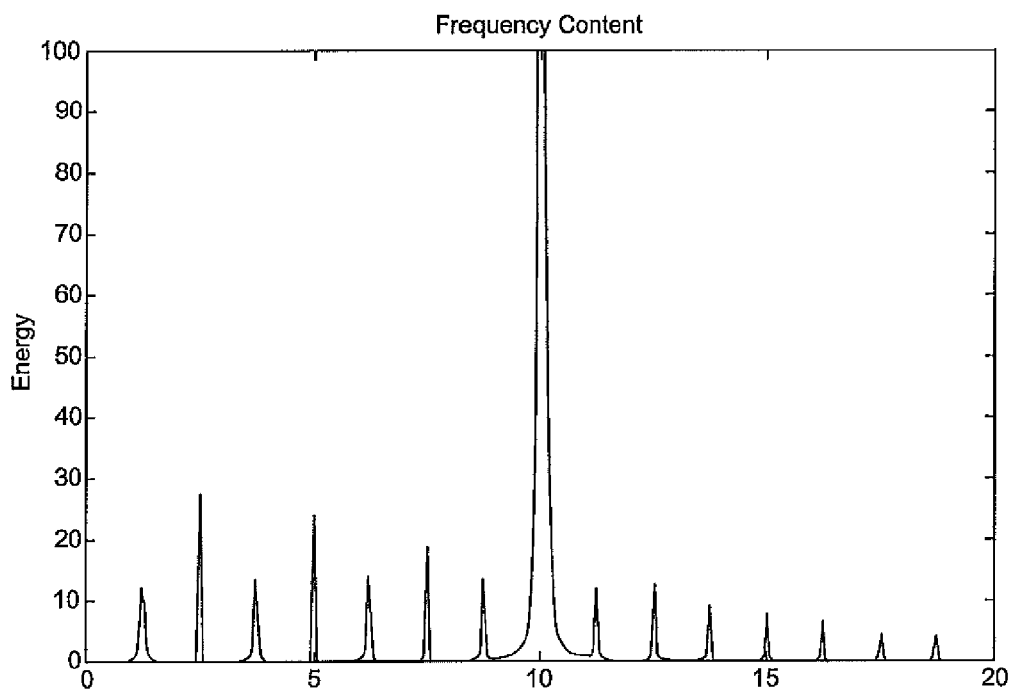
FIG. 9 is an expanded view of a frequency domain plot of FIG. 8 having undesirable energy peaks from zero to twenty of a frequency content.

FIGS. 6-9 show waveforms and frequency domain plots of exemplary signals. FIG. 6 is an expanded view of a sinusoid wave of un-modulated timing of the frame synchronization signal 240. FIG. 7 is an expanded view of the frequency domain plot of the un-modulated timing and frame synchronization signals 235, 240 in accordance with an embodiment of the present disclosure. FIG. 8 is a sinusoid wave and a frame modulation that is generated, for example, every 8 cycles, of the modulated timing of the frame synchronization signals 240. FIG. 9 is an expanded view of a frequency domain plot of FIG. 8 showing undesirable energy peaks from zero to twenty of a frequency content.

Figure 10:
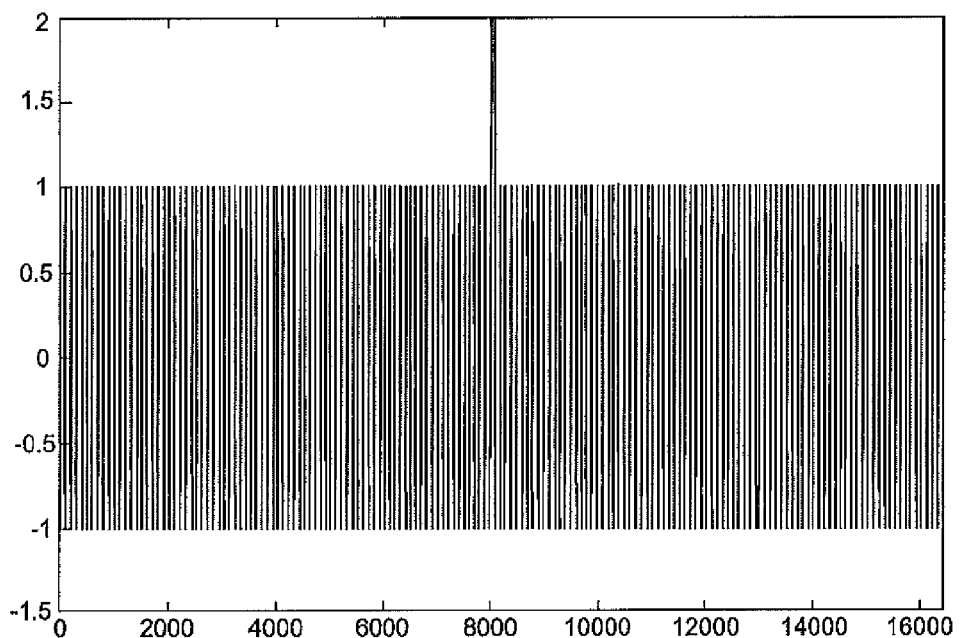
FIG. 10 is a sinusoid wave and a suppressed frame modulation that is generated by a PET processing device, such as that shown in FIG. 2.
Figure 11:
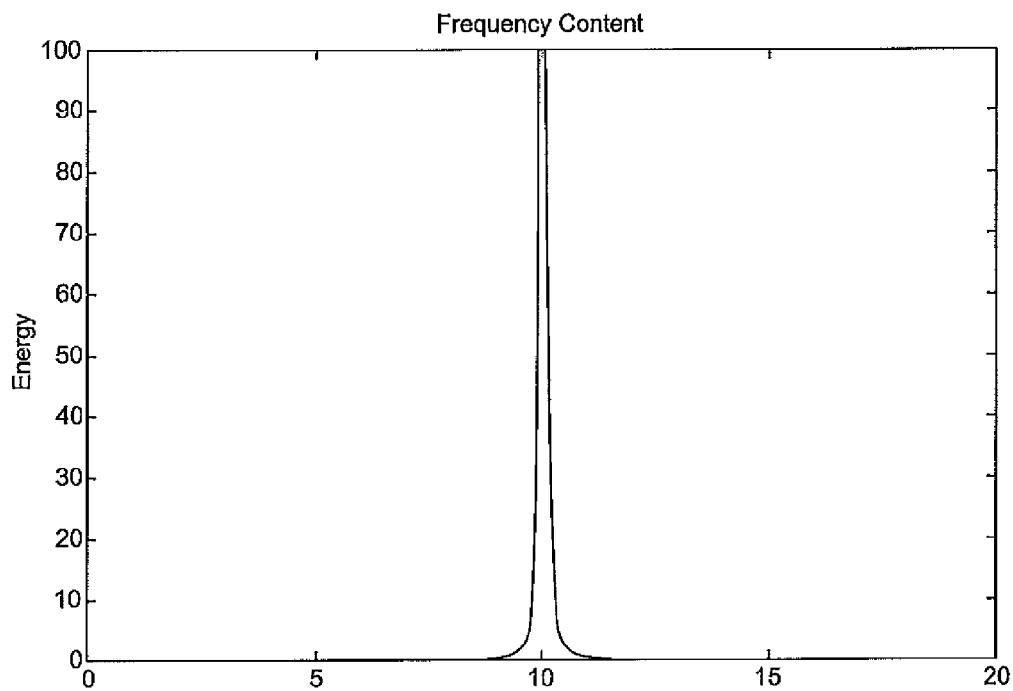
FIG. 11 is an expanded view of the frequency domain plot of FIG. 10.

FIGS. 10 and 11 show waveforms and frequency domain plots of modulated signals, resulting in reduced to no interference to the MR receiver 215 (FIG. 2) of the MR detector device 135 (FIG. 1). FIG. 10 is a sinusoid wave and a suppressed frame modulation that is generated by a PET processing device 230, such as that shown in FIG. 2. FIG. 11 is an expanded view of the frequency domain plot of FIG. 10, showing only one peak from zero to twenty of the frequency content of the fundamental frequency of the sinusoid. FIG. 11 shows that the present disclose can achieve a frequency domain plot that is similar to the frequency domain plot of FIG. 7 despite having modulated timing of the frame synchronization signal 240. It should be noted that the frequency domain plot of FIG. 7 is a frequency domain plot resulted from un-modulated timing of the frame synchronization signal 240. As such, the MR detector device 135 cannot operate at the frequency content of 10 KHz, but can operate in the range of 0 to about 10 KHz and from about 10 to 20 KHz with little to no interference from the PET detector device 105.

Figure 12:
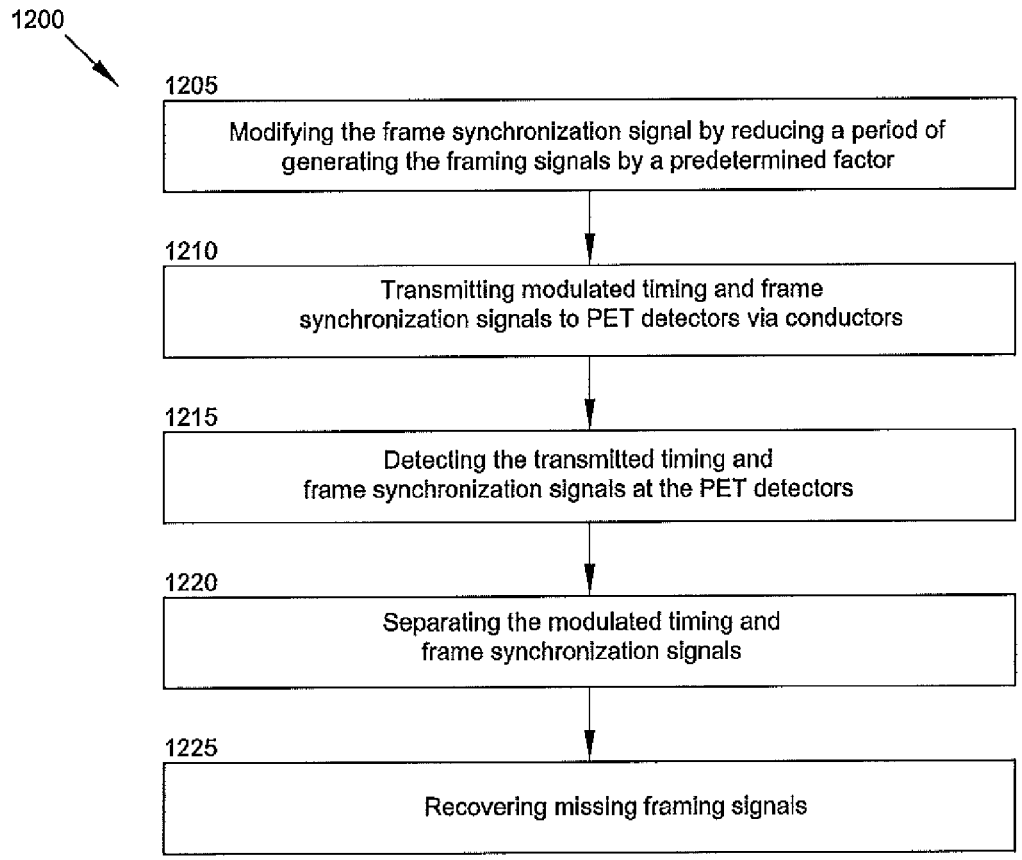
FIG. 12 is a flow diagram that illustrates an embodiment of the architecture, functionality, and/or operation of a MR-PET dual modality system 10 in accordance with an embodiment of the present disclosure.

FIG. 12 is a flow diagram 1200 that that illustrates an embodiment of the architecture, functionality, and/or operation of a MR-PET dual modality system 100 in accordance with an embodiment of the present disclosure. Beginning with block 1205, a PET processing device 230 modifies the frame synchronization signal 240 by reducing a period of generating the framing signals 310 by a predetermined factor. Alternatively or additionally, the PET processing device 230 can modify the frame synchronization signal 240 to generate the framing signals 310 once per predetermined number of transitions of the timing signal 235. Alternatively or additionally, the PET processing device 230 can suppress the framing signals 310 for a period based upon a multiplication of pre-determined number of transitions of the timing signal 235 and a predetermined period of the framing signals 310.

In block 1210, the PET processing device 230 transmits modulated timing and frame synchronization signals 235, 240 to the PET detectors 220 via metallic conductors 225. In block 1215, the PET processing device 230 detects the transmitted timing and frame synchronization signals 235, 240 at the PET detectors 220. The transmitted frame synchronization signal 235, 240 includes missing framing signals 315.

In block 1220, the framing recovery device 127 separates the modulated timing and frame synchronization signals 235, 240. In block 1225, the framing recovery device 127 recovers the framing signals 310 that were missing in the frame synchronization signal 415.

It should be noted that any process descriptions or blocks in flowcharts should be understood as representing modules, segments, or portions of code which include one or more executable instructions for implementing specific logical functions or steps in the process. As would be understood by those of ordinary skill in the art of the software development, alternate embodiments are also included within the scope of the disclosure. In these alternate embodiments, functions may be executed out of order from that shown or discussed, including substantially concurrently or in reverse order, depending on the functionality involved.

The systems and methods disclosed herein can be implemented in software, hardware, or a combination thereof. In some embodiments, the system and/or method is implemented in software that is stored in a memory and that is executed by a suitable microprocessor (μP) situated in a computing device. However, the systems and methods can be embodied in any computer-readable medium for use by or in connection with an instruction execution system, apparatus, or device. Such instruction execution systems include any computer-based system, processor-containing system, or other system that can fetch and execute the instructions from the instruction execution system. In the context of this disclosure, a "computer-readable medium" can be any means that can contain, store, communicate, propagate, or transport the program for use by, or in connection with, the instruction execution system. The computer readable medium can be, for example, but not limited to, a system or propagation medium that is based on electronic, magnetic, optical, electromagnetic, infrared, or semiconductor technology.

Specific examples of a computer-readable medium using electronic technology would include (but are not limited to) the following: an electrical connection (electronic) having one or more wires; a random access memory (RAM); a read-only memory (ROM); an erasable programmable read-only memory (EPROM or Flash memory). A specific example using magnetic technology includes (but is not limited to) a portable computer diskette. Specific examples using optical technology include (but are not limited to) optical fiber and compact disc read-only memory (CD-ROM).

Note that the computer-readable medium could even be paper or another suitable medium on which the program is printed. Using such a medium, the program can be electronically captured (using, for instance, optical scanning of the paper or other medium), compiled, interpreted or otherwise processed in a suitable manner, and then stored in a computer memory. In addition, the scope of the certain embodiments of the present disclosure includes embodying the functionality of the preferred embodiments of the present disclosure in logic embodied in hardware or software-configured mediums.

This description has been presented for purposes of illustration and description. It is not intended to be exhaustive or to limit the disclosure to the precise forms disclosed. Obvious modifications or variations are possible in light of the above teachings. The embodiments discussed, however, were chosen to illustrate the principles of the disclosure, and its practical application. The disclosure is thus intended to enable one of ordinary skill in the art to use the disclosure, in various embodiments and with various modifications, as are suited to the particular use contemplated. All such modifications and variation are within the scope of this disclosure, as determined by the appended claims when interpreted in accordance with the breadth to which they are fairly and legally entitled.

Therefore, having thus described the disclosure, at least the following is claimed:

1. A magnetic resonance (MR)-positron emission tomography (PET) device dual modality system, comprising:
    a dual modality detector system including a PET detector device having a demodulator and counter and a plurality of PET detectors, and an MR detector device having a magnetic resonance (MR) receiver;
    conductors that are electrically connected to the plurality of PET detectors;
    MR coils positioned with respect to the conductors of the plurality of PET detectors such that said MR coils are subject to interference by spectral radiation from said conductors;
    a microprocessor and associated software which transmits modulated timing and frame synchronization signals to the PET detectors through said conductors, wherein the frame synchronization signal includes one or more missing framing signals, thereby reducing a spectral radiation of the conductors that causes interference to the MR receiver of the MR detector device, wherein the demodulator and counter detects the transmitted timing and frame synchronization signals at the PET detectors, and recovers the one or more missing framing signals.

2. The MR-PET dual modality system of claim 1, wherein the demodulator separates the PET timing and PET frame synchronization signals.

3. The MR-PET dual modality system of claim 1, wherein the demodulator includes an amplitude demodulator.

4. The MR-PET dual modality system of claim 1, wherein the counter recovers one or more missing framing signals by detecting a framing signal from the transmitted PET timing and PET frame synchronization signals, counting cycles of the PET timing signal from the detected PET framing signal, and generating one or more framing signals at every predetermined number of cycles of the PET timing signal.

5. The MR-PET dual modality system of claim 1, wherein the PET processing device modifies the frame synchronization signal to reduce a period of generating framing signals by a predetermined factor.

6. The MR-PET dual modality system of claim 1, wherein the microprocessor and associated software modifies the frame synchronization signal to generate framing signals once per predetermined number of transitions of the timing signal.

7. The MR-PET dual modality system of claim 1, wherein the microprocessor and associated software suppresses framing signals for a period based upon a multiplication of predetermined number of transitions of the timing signal and a predetermined period of the framing signals.

8. A method for reducing interference in a magnetic resonance (MR)-positron emission tomography (PET) device dual modality system, wherein the MR-PET device dual modality system includes a dual modality detector system that includes a PET detector device having a framing recovery device and a plurality of PET detectors, and an MR detector device having a magnetic resonance (MR) receiver, wherein the PET detectors are connected to a PET processing device via conductors, the method comprising:
    transmitting modulated timing and frame synchronization signals by the PET processing device to the PET detectors, wherein the frame synchronization signal includes one or more missing framing signals, thereby reducing a spectral radiation of the conductors that causes interference to the MR receiver of the MR detector device;
    detecting the transmitted timing and frame synchronization signals by the framing recovery device at the PET detectors; and
    recovering the one or more missing framing signals by the framing recovery device.

9. The method of claim 8, wherein recovering the one or more missing framing signals includes the steps of:
    detecting a framing signal from the transmitted timing and frame synchronization signals;
    counting cycles of the timing signal from the detected framing signal; and
    generating one or more framing signals at every predetermined number of cycles of the timing signal.

10. The method of claim 8, further comprising separating the modulated timing and frame synchronization signals.

11. The method of claim 8, further comprising modifying the frame synchronization signal by reducing a period of generating framing signals by a predetermined factor.

12. The method of claim 8, further comprising modifying the frame synchronization signal to generate framing signals once per predetermined number of transitions of the timing signal.

13. The method of claim 8, further comprising suppressing framing signals for a period based upon a multiplication of predetermined number of transitions of the timing signal and a predetermined period of the framing signals.

14. A magnetic resonance (MR)-positron emission tomography (PET) device dual modality system, comprising:
    a dual modality detector system including a PET detector device having a demodulator and counter and a plurality of PET detectors, and an MR detector device having a magnetic resonance (MR) receiver and an MR coil, wherein the MR coil and the MR receiver are located in the proximity of the PET detectors, respectively;
    conductors that are electrically connected to the PET detectors; and
    a microprocessor and associated software which transmits modulated timing and frame synchronization signals to the PET detectors through said conductors, wherein the frame synchronization signal includes one or more missing framing signals, thereby reducing a spectral radiation of the conductors that causes interference to the MR receiver of the MR detector device, wherein the demodulator and counter detects the transmitted timing and frame synchronization signals at the PET detectors, and recovers the one or more missing framing signals.

15. The MR-PET dual modality system of claim 14, wherein the demodulator separates the modulated PET timing and PET frame synchronization signals.

16. The MR-PET dual modality system of claim 14, wherein the demodulator includes an amplitude demodulator.

17. The MR-PET dual modality system of claim 14, wherein the counter that recovers the one or more missing framing signals by detecting a framing signal from the transmitted PET timing and PET frame synchronization signals, counting cycles of the timing signal from the detected framing signal, and generating one or more framing signal at every predetermined number of cycles of the PET timing signal.

18. The MR-PET dual modality system of claim 14, wherein the microprocessor and associated software modifies the PET frame synchronization signal to reduce a period of generating framing signals by a predetermined factor.

19. The MR-PET dual modality system of claim 14, wherein the microprocessor and associated software modifies the PET frame synchronization signal to generate framing signals once per predetermined number of transitions of the PET timing signal.

20. The MR-PET dual modality system of claim 14, wherein the microprocessor and associated software suppresses framing signals for a period based upon a multiplication of predetermined number of transitions of the PET timing signal and a predetermined period of the PET framing signals.

* * * * *